United States Patent [19]
Kido et al.

[11] Patent Number: 5,900,401
[45] Date of Patent: May 4, 1999

[54] REMEDY FOR RESPIRATORY-TRACT VIRAL DISEASE

[75] Inventors: Hiroshi Kido, Tokushima; Masato Tashiro; Shozaburo Sekido, both of Tokyo, all of Japan

[73] Assignee: Tokyo Tanabe Company Limited, Tokyo, Japan

[21] Appl. No.: 08/716,404

[22] PCT Filed: Mar. 20, 1995

[86] PCT No.: PCT/JP95/00513

§ 371 Date: Nov. 7, 1996

§ 102(e) Date: Nov. 7, 1996

[87] PCT Pub. No.: WO95/25539

PCT Pub. Date: Sep. 28, 1995

[30] Foreign Application Priority Data

Mar. 23, 1994 [JP] Japan ..................... 6-052237

[51] Int. Cl.$^6$ ............ A61K 38/55; C07K 14/81
[52] U.S. Cl. ............... 514/2; 514/12; 530/350; 424/211.1; 424/212.1
[58] Field of Search ............ 514/12, 2; 530/324, 530/350

[56] References Cited

U.S. PATENT DOCUMENTS

| | | | |
|---|---|---|---|
| 4,760,130 | 7/1988 | Thompson et al. | 530/350 |
| 4,845,076 | 7/1989 | Heinzel et al. | 514/12 |
| 5,290,762 | 3/1994 | Lezdey et al. | 514/8 |
| 5,633,227 | 5/1997 | Muller et al. | 514/12 |

FOREIGN PATENT DOCUMENTS

| | | |
|---|---|---|
| 2002047 | 6/1990 | Canada . |
| 62-259591 | 11/1987 | Japan . |
| 3-123490 | 5/1991 | Japan . |
| 86/03519 | 6/1986 | WIPO . |
| WO 86/03497 | 6/1986 | WIPO . |
| 89/06239 | 7/1989 | WIPO . |
| 94/00181 | 1/1994 | WIPO . |
| WO 94/00131 | 1/1994 | WIPO . |

OTHER PUBLICATIONS

Rudinger, J. (1976). Peptide Hormones (ed. J.A. Parsons). University Park Press. Baltimore. pp. 1–7, 1976.

Hiroshi Kido et al., the Journal of Biological Chemistry, vol. 267, No. 19 (1992), pp. 13573–13579.

Grutter, et al., "The 2.5 ÅA X–ray crystal structure of the acid–stable proteinase inhibitor from human mucous secretions analysed in its complex with bovine α–chymotrypsin", The EMBO Journal vol. 7, No.2, pp.345–351 (1988).

Tashiro, et al., "Tryptase Clara, an Activating Protease for Sendai Virus in Rat Lungs, Is Involved in Pneumopathogenicity", Journal of Virology, Dec. 1992, pp. 7211–7216.

Kido, et al., "Pulmonary surfactant is a potential endogenous inhibitor of proteolytic activation of Sendai virus and influenza A virus", FEBS Letters, vol. 322, No. 2, 115–119 (1993).

*Primary Examiner*—Cecilia J. Tsang
*Assistant Examiner*—Anish Gupta
*Attorney, Agent, or Firm*—Griffin, Butler Whisenhunt & Szipl, LLP

[57] ABSTRACT

The present invention is a therapeutic or prophylactic agent for viral diseases whose active ingredient is antileukoprotease (ALP). Formulations containing ALP as an active ingredient have particularly effective application against viral diseases, particularly viral diseases caused by viruses which are activated by tryptase Clara, i.e. viruses with envelope glycoproteins, which replicate by infection of the respiratory-tract, such as influenza virus, parainfluenza virus, RS virus, measles virus and mumps virus.

47 Claims, 4 Drawing Sheets

1. [³H] Glucosamine labeled Influenza A/Aichi/2/68 (H3N2) + Tryptase Clara (50 μg/ml)
2. 1 + 10nM ALP
3. 1 + 100nM ALP
4. 1 + 1 μM ALP

REMEDY FOR RESPIRATORY-TRACT VIRAL DISEASE

This application is a 371 of PCT/JP95/00513, filed Mar. 20, 1995.

FIELD OF THE INVENTION

The present invention relates to a therapeutic or prophylactic agent for viral diseases, whose active ingredient is antileukoprotease (hereunder, ALP). More specifically, it relates to a therapeutic or prophylactic agent containing ALP as an active ingredient for respiratory-tract viral diseases caused by the viruses which are activated by tryptase Clara.

BACKGROUND OF THE INVENTION

ALP is present in external secretions such as bronchial mucous, saliva, seminal fluid, cervical mucous and nasal discharge, and it is a serine protease inhibitor with a molecular mass of 12 kDa consisting of 107 amino acid residues, which is considered to be the same substance as secretory leukoprotease inhibitor (SLPI), bronchial mucous inhibitor, mucous protease inhibitor and human seminal inhibitor. The amino acid sequence of ALP has been determined (WIPO Publication No. WO86/03497), and the protein's gene has been isolated and sequenced (WIPO Publication No. WO86/03519).

From homology comparisons, ALP is known to comprise two inhibitor domains. One is an N-terminal domain which is postulated to inhibit various trypsin-like enzymes, and the other is a C-terminal domain which from X-ray crystal structure analysis research is believed to bind to chymotrypsin and has an elastase-inhibiting activity. [M. G. Gruetter, The EMBO. Journal, Vol.7, No.2, pp.345–351 (1988)].

Since ALP inhibits chymotrypsin-like enzymes such as leukocyte elastase and cathepsin G and also inhibits trypsin-like enzymes such as trypsin, plasmin, kallikrein and thrombin, etc., it is known to be connected with emphysema, arthritis, glomerular nephritis, periodontitis, muscular atrophy, tumor invasion (WIPO Publication No. WO86/03497), chronic bronchitis, and chronic cervical inflammation (Japanese Unexamined Patent Publication No. 62-259591). However, the role of ALP in viral diseases is still unknown.

Viral infections occur through the steps of 1) attachment of a virus to membrane receptors on the target cells, 2) membrane fusion between the virus envelope and the target cell membrane, and 3) transfusion of the viral genome into the target cells. In the step 2) of membrane fusion, viral envelope glycoprotein precursors have to be converted to the mature form of virus envelope glycoproteins with membrane fusion activity. After this conversion by proteolysis, the virus acquires the activity of membrane fusion between the virus envelopes and cell membranes in the respiratory-tract. Hemagglutinin (HA) of influenza virus and $F_0$ of Sendai virus (Paramyxovirus parainfluenza virus Type I) are the envelope glycoprotein precursors, and their proteolytic cleavage is essential for expression of viral infectivity and for the viral replication.

The present inventors have succeeded in isolating a novel arginine-specific serine protease from rat lungs, which has been named "tryptase Clara" (The Journal of Biological Chemistry, Vol.267, pp.13573–13579, 1992).

Tryptase Clara cleaves the $F_0$ of Sendai virus into two subunits $F_1$ and $F_2$, and activates infectivity of the virus in vitro in a dose-dependent manner. In addition, antibodies against tryptase Clara are known to inhibit the proteolytic activation of Sendai virus in rat lungs, resulting in the suppression of the viral replication and pathological changes in rat lungs (Journal of Virology, Vol.66, pp.7211–7216, 1992).

Furthermore, tryptase Clara also cleaves the HA of influenza A/Aichi/2/68(H3N2) virus into $HA_1$ and $HA_2$ (The Journal of Biological Chemistry, Vol.267, pp.13573–13579, 1992).

Taken together, tryptase Clara is believed to be a principal host factor which determines the pathogenicity of such contagious viruses in the respiratory-tract.

The present inventors have previously discovered that pulmonary surfactant inhibits the cleavage by tryptase Clara of virus envelope glycoprotein precursors, and thus blocks the viral infection of bronchial mucous epithelial cells and viral replication (WIPO Publication No. WO94/00181, FEBS Letters, 322, 115–119 (1993)).

SUMMARY OF THE INVENTION

As a result of continued research by the present inventors for the purpose of finding a substance which inhibits activation of viruses by tryptase Clara, it was found that ALP is able to notably inhibit viral activation by tryptase Clara and thus inhibit replication of viruses in virus-infected animals, and the present invention was thereby completed.

The present invention provides a therapeutic and prophylactic agent for viral diseases which contains ALP as an active ingredient thereof.

The ALP used according to the invention includes not only ALP isolated and purified from natural sources and ALP produced by genetic engineering methods (for example, by the methods described in WIPO Patent Publications WO86/03519, WO89/06239, Japanese Unexamined Patent Publication Nos. 62-259591, No.3-123490, etc.), but also proteins consisting of ALP with a substitution, deletion, insertion or addition at some portion of the amino acid sequence, which exhibit the same activity as ALP.

The viral diseases to be targeted by the therapeutic or prophylactic agent of the invention include viral diseases caused by influenza virus, paramyxovirus, respiratory syncytial virus (hereunder, "RS virus"), rhinovirus, coronavirus, reovirus, adenovirus, Coxsackie virus, echovirus, simple herpes virus, rotavirus, enterovirus, poliovirus, cytomegalovirus, varicella zoster virus and HIV, but are preferably viral diseases in which infection occurs in the respiratory-tract due to viruses activated by tryptase Clara, i.e. enveloped viruses, such as influenza virus, paramyxovirus, RS virus, measles virus and mumps virus.

and the extent of lung damage in "B". In "A", the solid line represents virus titer in the absence of ALP, and the broken line represents the same in the presence of ALP, while the open circles represent total virus titer and the closed circles represent active virus titer. ALP was administered at the points indicated by arrows.

DESCRIPTION OF THE PREFERRED EMBODIMENTS

The effect of ALP on viral diseases will be described. The following ALP, viruses and tryptase were used in each experiment.

ALP

Natural ALP was used, prepared according to the method described in Japanese Unexamined Patent Publication No. 62-259591.

Viruses

The viruses used were Sendai virus and influenza virus [influenza A/Aichi/2/68 (H3N2) virus and mouse-adapted influenza A/Asia/1/57 (H2N2) virus]. Sendai and influenza viruses grown in the amniotic cavity of developing hen's eggs were each suspended in a calcium-free phosphate buffer solution in a proportion of 254 HAU/ml (hemagglutination units/ml).

Tryptase Clara

Tryptase Clara was prepared from rat lungs, according to the method of Kido (The Journal of Biological Chemistry, Vol.267, pp.13573–13579, 1992).

Rat lungs were washed with physiological saline and then minced with scissors, homogenized at pH 5.5, and centrifuged to obtain a supernatant solution which was used as the extract. This raw extract was then subjected to ion exchange column chromatography in a CM-52 Cellulose column (trade name) and a CM-52 Sephadex column (trade name), and the fractions with an activity measured with Boc-Gln-Ala-Arg-MCA as a substrate were collected. The collected active fractions were subjected to an affinity chromatography on an arginine-Sepharose column (trade name) which is a serine protease specific adsorbent. The trypsin-like enzyme in the eluate was collected by specific adsorbtion. Finally, this enzyme solution was subjected to a gel filtration column and the active fractions were collected for isolation and purification to prepare tryptase Clara.

Test of viral protein cleavage inhibition by ALP (EXAMPLE 1: - Sendai virus)

The test was conducted according to the method described in The Journal of Virology, Vol.66, pp.7211–7216, 1992.

Figure 1:
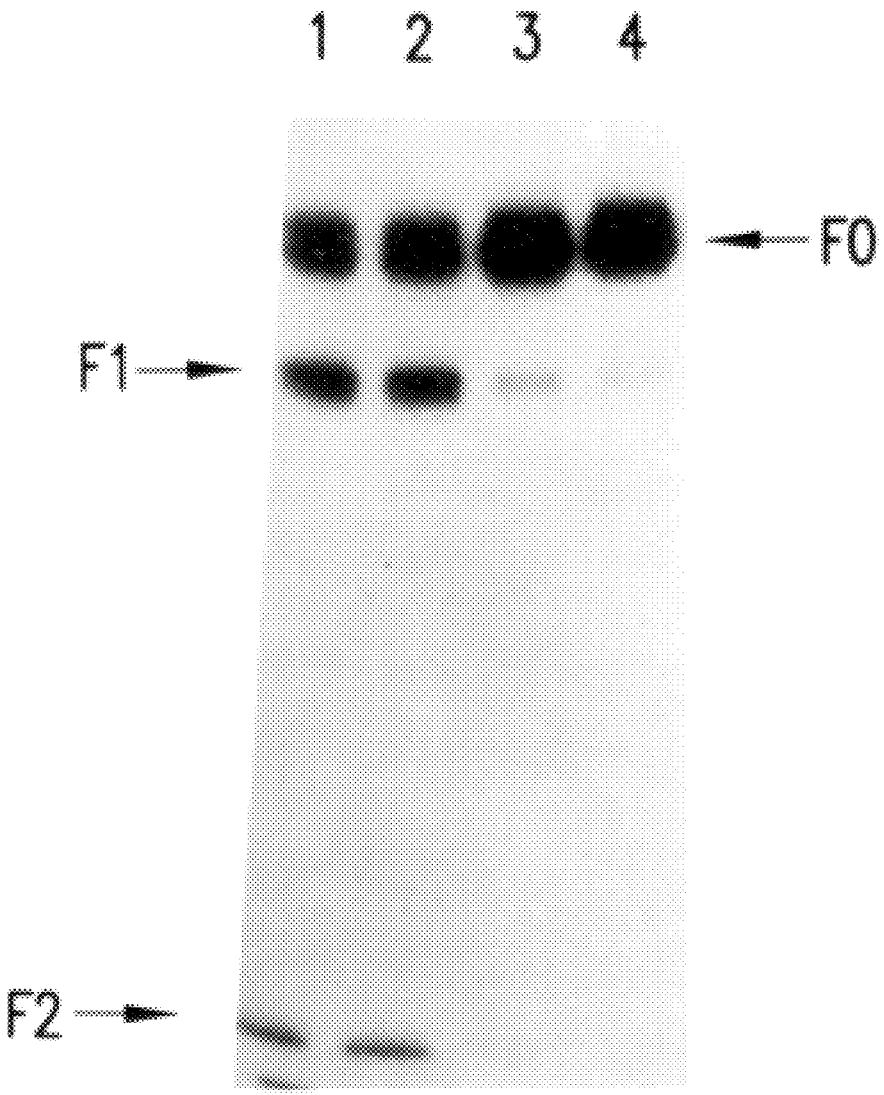
FIG. 1 shows the inhibitory effect of ALP on the cleavage of Sendai virus envelope glycoprotein precursor $F_0$ by tryptase Clara.

Tryptase Clara (50 $\mu$g/ml) and various concentrations of ALP (10 nM, 100 nM and 1 $\mu$M) dissolved in distilled water were preincubated for 5 minutes at 0° C., and then the cleavability of the $F_0$ protein of [$^3$H] glucosamine-labelled inactive Sendai virus grown in LLC-MK$_2$ cells was determined. The results of analysis by sodium dodecyl sulfate-polyacrylamide electrophoresis are shown in FIG. 1.

It was found that ALP inhibits cleavage of $F_0$ by tryptase Clara into subunits $F_1$ and $F_2$ in a dose-dependent manner, with 100% inhibition at 1 $\mu$M.

(EXAMPLE 2: - Influenza virus)

The cleavage of HA protein of the influenza virus (influenza A/Aichi/2/68 (H3N2) virus) into HA$_1$ and HA$_2$ by tryptase Clara was investigated according to the method described in The Journal of Biological Chemistry, Vol.267, pp.13573–13579, 1992 and Example 1

Figure 2:
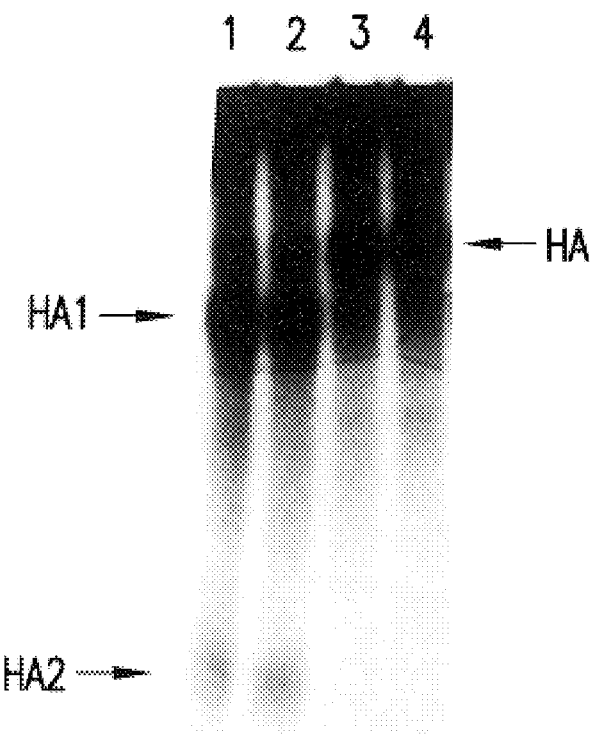
FIG. 2 shows the inhibitory effect of ALP on the cleavage of influenza virus envelope glycoprotein precurser HA by tryptase Clara.

As shown in FIG. 2, ALP inhibits the cleavage of HA into subunits HA$_1$ and HA$_2$ by tryptase Clara in a dose-dependent manner.

Test of the inhibition of viral infection by ALP (in vitro)

(EXAMPLE 3: -Sendai virus)

This test was conducted according to the method described in WIPO Publication WO94/00131. Tryptase Clara (20 $\mu$g/ml) was preincubated with various concentrations (0.1, 10, 100 and 1000 nM) of ALP in physiological saline at 0° C. for 20 minutes. Then, inactive Sendai virus grown in LLC-MK$_2$ cells was treated with the reaction mixture at 37° C. for 5 minutes. The reaction was terminated by aprotinin (100 $\mu$g/ml). Active Sendai virus obtained by this treatment was again added to LLC-MK$_2$ cells which were then cultured for 15 hours, after which the CIU (Cell Infecting Unit) was measured by the immunofluorescent cell counting method. Viral infectivity was expressed as CIU titer ($\log_{10}$CIU/ml).

(EXAMPLE 4: - Influenza virus: Influenza A/Aichi/2/68(H3N2) virus)

Treatment, CIU measurement and determination of viral infectivity titer were accomplished in the same manner as Example 3, except that influenza virus (Influenza A/Aichi/2/68(H3N2) virus) was used instead of Sendai virus and MDCK cells were used instead of LLC-MK$_2$ cells.

Figure 3A:
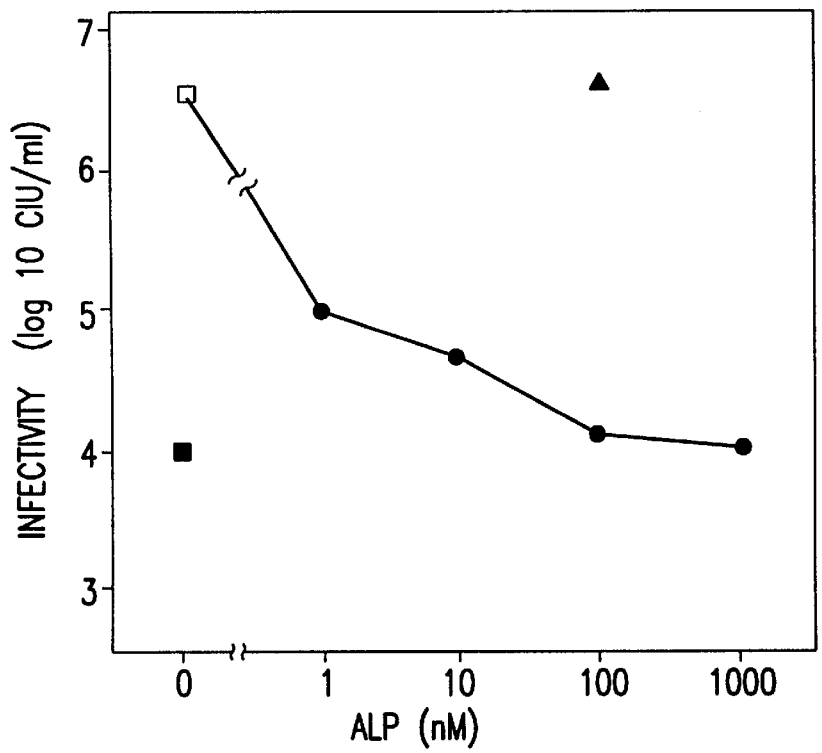
FIG. 3 shows the inhibitory effect of ALP on the infection with Sendai virus and influenza virus in cultured cells. The experiment of the infection with Sendai virus is shown in FIG. 3 "A" and that with influenza virus in FIG. 3 "B".
Figure 3B:
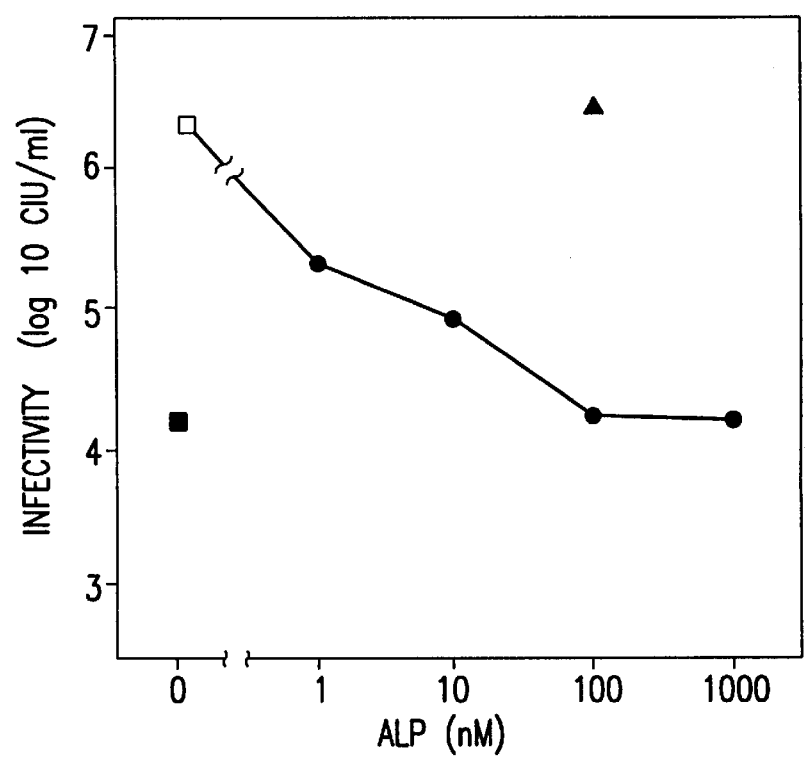

FIG. 3 shows the inhibitory effect of ALP on the infection with Sendai virus and influenza virus. Inactive viruses prior to treatment with tryptase Clara were ($1\times10^4$ CIU/ml and $1.2\times10^4$ CIU/ml, respectively) activated by tryptase Clara up to $4\times10^6$ CIU/ml and $1.8\times10^8$ CIU/ml, respectively.

ALP reduced both viral infectivities by addition of ALP (1 nM–1 $\mu$M) in a dose-dependent manner and inhibited the cleavage of the viral envelope glycoprotein by tryptase Clara. Almost 100% inhibitory effect of ALP on the infection was observed at 100 nM–1 $\mu$M.

Test of inhibitory effect of ALP on viral infection (in vivo)

(EXAMPLE 5: - Animal experiments on anti-influenza effect of ALP)

The test was conducted according to the method described in Journal of Virology, Vol.66, pp.7211–7216, 1992.

Specifically, SD rats (3 weeks old, body weight: 120 g, product of Japan Charles River Co.) were intranasally infected with $1\times10^4$ plaque-forming units (PFU) of influenza virus (mouse-adapted influenza A/Asia/1/57(H2N2) virus). ALP was intranasally administered at 6 $\mu$g (50 $\mu$l) per rat once every 8 hours after infection for a total of 15 times. The control was administered 50 $\mu$l of physiological saline. At the indicated time, three rats were butchered every 24 hours, and the total virus and the active virus titer in the lung homogenates were measured.

The degree of total lung inflammation was expressed as a lung lesion score based on visual observation. The lung lesion score was a 5-level score from 0 to 4 representing the proportion of hepatization, i.e. brown area, with respect to total lung surface area. For the lung lesion score, 0 indicates 0% hepatization with respect to total lung surface area, 1 indicates 1–25%, 2 indicates 26–50%, 3 indicates 51–75% and 4 indicates 76–100%.

Figure 4A:
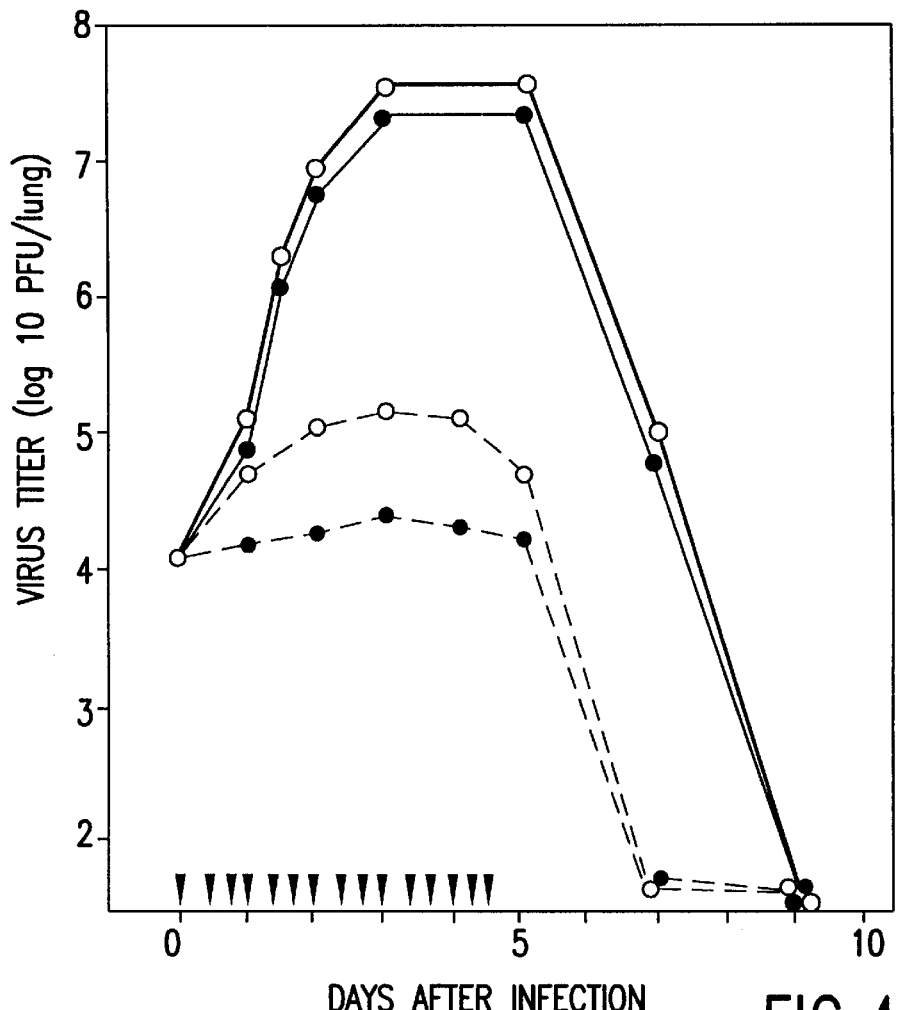
FIG. 4 shows the effect of ALP on rats infected with influenza virus (mouse-adapted influenza A/Asia/1/57 (H2N2) virus). The virus titer in the lung is shown in "A"
Figure 4B:
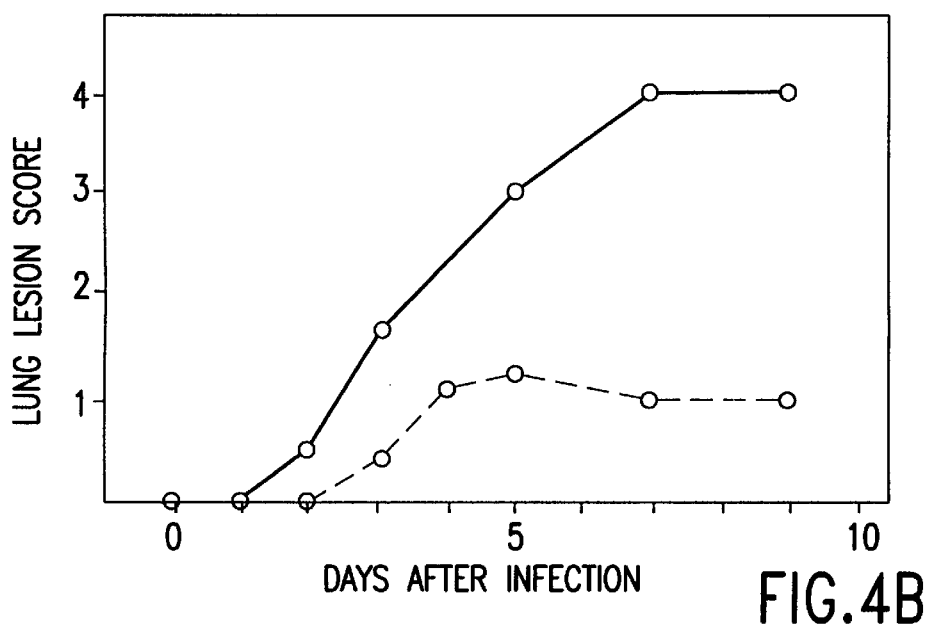

The results are summarized in FIG. 4.

The rats infected with the influenza virus (mouse-adapted influenza A/Asia/1/57(H2N2) virus) and given physiological saline exhibited an increase in virus titer of about 2000-fold by the 5th day, of which at least 95% was active virus. Severe lung inflammation was observed, reached a peak on the 7th day, and continued to the 9th day.

In contrast, the rats which were intranasally administered ALP at 6 μg/rat for a total of 15 times exhibited only a small increase in virus titer of approximately 10-fold by the 5th day, which represented inhibition of the virus titer to a mere 0.5% of that observed with the group not treated with ALP. Furthermore, 95% of this only slightly increased virus remained inactive. The lung inflammation reached a peak on the 5th day with a score of 1, showing only minimal progression.

Thus, ALP clearly inhibited enlargement of lung lesions due to viral infection, demonstrating its effectiveness against growth of viral infection.

Method and Dosages

A single dosage of the therapeutic or prophylactic agent for viral diseases according to the invention contains ALP at 0.1 μg–500 mg, preferably 1 μg–100 mg and more preferably 10 μg–10 mg for infants and 0.5 μg–1000 mg, preferably 5 μg–500 mg and more preferably 50 μg–50 mg for adults. The dose is dissolved in an electrolytic solution such as an aqueous or physiological saline solution, the concentration is adjusted to 0.1–500 mg/ml, preferably 0.5–200 mg/ml and more preferably 1–100 mg/ml, and is infused or nebulized into the respiratory-tract, or used in the form of a collutory agent, either before viral infection or after outbreak of the viral disease.

The therapeutic or prophylactic agent of the invention may also contain if necessary pharmaceutical additives such as stabilizers, preservatives, isotonizing agents, buffering agents or suspending agents, or pharmaceutical agents such as bronchodilators, antitussive agents, anti-allergy agents, antipyretic analgesics, antibiotics, synthetic antibacterial agents or other anti-viral agents. The preparation may be in liquid form, or a powder or aerosol preparation which is suspended at the time of use, and may be filled into a vial, ampule or other sealed container as an antiseptic preparation.

Industrial Applicability

Thus, ALP notably inhibits activation of viruses by tryptase Clara, and thus impedes viral replication in animals infected with those viruses.

Consequently, formulations containing alp as an effective ingredient have effective application for viral diseases, particularly viral diseases caused by viruses which are activated by tryptase clara, i.e. viruses with envelope glycoproteins, which replicate by infection of the respiratory-tract, such as influenza virus, parainfluenza virus, RS virus, measles virus and mumps virus

What is claimed is:

1. A method for treating a mammal infected with a virus activated by Tryptase Clara:

comprising the step of administering to the mammal a medically effective dose of antileukoprotease.

2. A method according to claim 1, wherein the mammal is a human.

3. A method according to claim 1, wherein the effective amount is 0.1μ–500 mg.

4. A method according to claim 1, wherein the effective amount is 1μ–100 mg.

5. A method according to claim 1, wherein the effective amount is 10μ–10 mg.

6. A method according to claim 1, wherein the effective amount is 50μ–50 mg.

7. A method according to claim 1, wherein the effective amount is 0.5μ–1000 mg.

8. A method according to claim 1, wherein the step of administering comprises infusion into the respiratory tract of the mammal.

9. A method according to claim 1, wherein the step of administering comprises nebulization into the respiratory tract of the mammal.

10. A method for preventing a mammal from becoming infected with a virus activated by tryptase Clara:

comprising the step of administering to the mammal a prophylactically effective dose of antileukoprotease.

11. A method according to claim 10, wherein the mammal is a human.

12. A method according to claim 10, wherein the effective amount is 0.1μ–500 mg.

13. A method according to claim 10, wherein the effective amount is 1μ–100 mg.

14. A method according to claim 10, wherein the effective amount is 10μ–10 mg.

15. A method according to claim 10, wherein the effective amount is 50μ–50 mg.

16. A method according to claim 10, wherein the effective amount is 0.5–μ1000 mg.

17. A method according to claim 10, wherein the step of administering comprises infusion into the respiratory tract of the mammal.

18. A method according to claim 10, wherein the step of administering comprises nebulization into the respiratory tract of the mammal.

19. A method for treating a mammal infected with a virus selected from the group consisting of influenza virus, parainfluenza virus, RS virus, measles virus, and mumps virus: comprising the step of administering to the mammal a medically effective dose of antileukoprotease.

20. A method for preventing a mammal from becoming infected with a virus selected from the group consisting of influenza virus, parainfluenza virus, RS virus, measles virus or mumps virus: comprising the step of administering to the mammal a prophylactically effective dose of antileukoprotease.

21. A method according to claim 19, wherein the mammal is a human.

22. A method according to claim 19, wherein the effective amount is 0.1μ–500 mg.

23. A method according to claim 19, wherein the effective amount is 1μ–100 mg.

24. A method according to claim 19, wherein the effective amount is 10μ–10 mg.

25. A method according to claim 19, wherein the effective amount is 50μ–50 mg.

26. A method according to claim 19, wherein the effective amount is 0.5μ–1000 mg.

27. A method according to claim 19, wherein the step of administering comprises infusion into the respiratory tract of the mammal.

28. A method according to claim 19, wherein the step of administering comprises nebulization into the respiratory tract of the mammal.

29. A method according to claim 19, wherein the virus is an influenza virus.

30. A method according to claim 19, wherein the virus is a parainfluenza virus.

31. A method according to claim 19, wherein the virus is an RS virus.

32. A method in claim 19, wherein the virus is a measles virus.

33. A method according to claim 19 wherein the virus is a mumps virus.

34. A method according to claim 20, wherein the virus is a virus with an envelope glycoprotein, which replicates through infection of the respiratory tract.

35. A method according to claim 20, wherein the mammal is a human.

36. A method according to claim 20, wherein the effective amount is 0.1μ–500 mg.

37. A method according to claim 20, wherein the effective amount is 1μ–100 mg.

38. A method according to claim 20, wherein the effective amount is 10μ–10 mg.

39. A method according to claim 20, wherein the effective amount is 50μ–50 mg.

40. A method according to claim 20, wherein the effective amount is 0.5μ–1000 mg.

41. A method according to claim 20, wherein the step of administering comprises infusion into the respiratory tract of the mammal.

42. A method according to claim 20, wherein the step of administering comprises nebulization into the respiratory tract of the mammal.

43. A method according to claim 20, wherein the virus is an influenza virus.

44. A method according to claim 20, wherein the virus is a parainfluenza virus.

45. A method according to claim 20, wherein the virus is an RS virus.

46. A method according to claim 20, wherein the virus is a measles virus.

47. A method according to claim 20, wherein the virus is a mumps virus.

\* \* \* \* \*